United States Patent [19]
O'keefe

[11] Patent Number: 5,713,836
[45] Date of Patent: Feb. 3, 1998

[54] DEFORMABLE SPLINT

[76] Inventor: Martin S. O'keefe, 14157 Ezra La., Poway, Calif. 92064

[21] Appl. No.: 638,744

[22] Filed: Apr. 29, 1996

[51] Int. Cl.⁶ .................................................. A61F 5/00
[52] U.S. Cl. ............................... 602/5; 602/20; 602/21
[58] Field of Search ........................ 602/5, 6, 20, 21, 602/22, 60, 63; 473/214, 60, 61, 62, 59, 212; 2/16, 18, 19, 20, 159, 160, 161.1–161.8; 128/878, 879

[56] References Cited

U.S. PATENT DOCUMENTS

| | | | |
|---|---|---|---|
| 1,867,258 | 7/1932 | Fruehauf | 602/22 |
| 2,703,082 | 3/1955 | Emert | 473/214 |
| 3,170,460 | 2/1965 | Stilson | 602/22 |
| 3,513,842 | 5/1970 | Keenan et al. | 602/63 |
| 4,270,528 | 6/1981 | Hanson | 602/22 |
| 4,615,522 | 10/1986 | Plough | 482/48 |

*Primary Examiner*—Richard J. Apley
*Assistant Examiner*—Kim M. Lee

[57] ABSTRACT

The present invention relates to an improved deformable splint which is adapted for engagement with the hand of a user. In its broadest context, the present invention includes a wire which is surrounded by a cover of resilient material. As such, the splint can be deformed into any number of various shapes to enable it to be employed upon the hand of the user in a number of different configurations. The splint further includes a number of VELCRO™ straps which are employed in securing the splint to the hand of a user. The various components of the present invention, and the manner in which they interrelate, will be described in greater detail hereinafter.

5 Claims, 3 Drawing Sheets

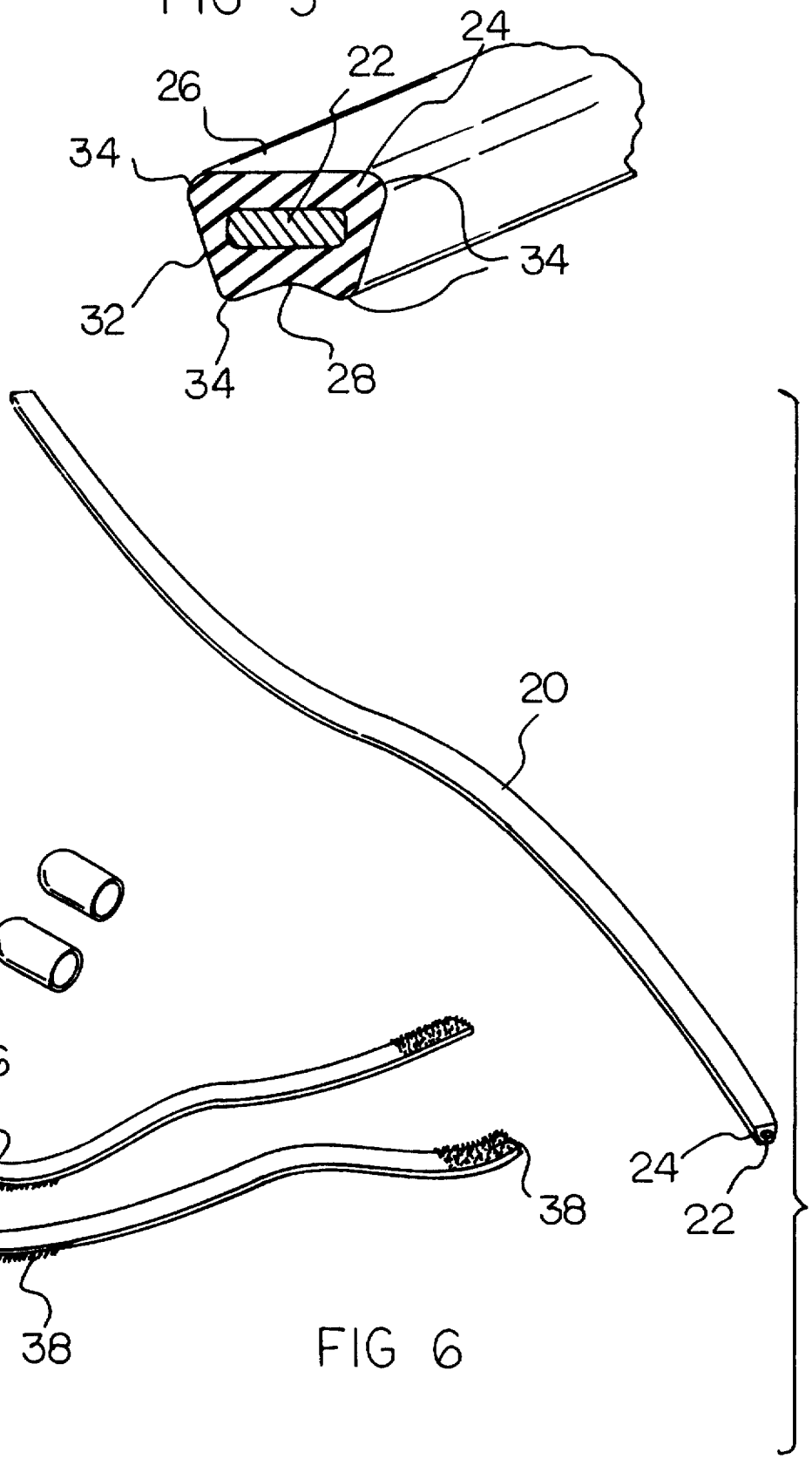

DEFORMABLE SPLINT

BACKGROUND OF THE INVENTION

1. Field of the Invention

The present invention relates to deformable splint and more particularly pertains to a splint which may be deformed.

2. Description of the Prior Art

The use of splints is known in the prior art. More specifically, splints heretofore devised and utilized for the purpose of healing portions of the hand are known to consist basically of familiar, expected, and obvious structural configurations, notwithstanding the myriad of designs encompassed by the crowded prior art which has been developed for the fulfillment of countless objectives and requirements.

By way of example, U.S. Pat. Nos. 5,417,645 to Lemmen; 5,205,812 to Wasserman; 5,058,576 to Grim et al; 5,230,699 to Grasinger; Des. 293,379 to Link; and Des. 292,128 all disclose various splints for use on the finger, hand or wrist.

In this respect, the deformable splint according to the present invention substantially departs from the conventional concepts and designs of the prior art, and in doing so provides an apparatus primarily developed for the purpose of providing a splint which may be deformed.

Therefore, it can be appreciated that there exists a continuing need for new and improved deformable splint which can be used for maintaining the wrist, hand or figure is a therapeutic orientation. In this regard, the present invention substantially fulfills this need.

SUMMARY OF THE INVENTION

In view of the foregoing disadvantages inherent in the known types of splints now present in the prior art, the present invention provides an improved deformable splint. As such, the general purpose of the present invention, which will be described subsequently in greater detail, is to provide a new and improved deformable splint and method which has all the advantages of the prior art and none of the disadvantages.

To attain this, the present invention essentially comprises a deformable splint which is adapted for a variety of supporting configurations upon a user's hand. The splint includes a length of heavy gauge copper wire, with the length of wire having a rectangular cross section, a first end, a second end, and an intermediate extent therebetween. The splint further includes a resilient cover constructed of neoprene. This cover is positioned over and covers the entire length of the wire. The cover includes a planar upper surface, a concave lower surface, two tapering side walls and four rounded corners which serve to interconnect the side walls and upper and lower surfaces. The cover is defined by a first end, a second end and an intermediate extent therebetween. A first securing strap is included with the splint. The strap is defined by a first end, a second end and an intermediate extent therebetween. The first and second ends each have hook and pile fasteners secured thereon. This first securing strap is adapted to couple the splint to a portion of the user's hand and to be secured thereon by way of the hook and pile fasteners. A second securing strap is also included which is defined by a first end, a second end and an intermediate extent therebetween. Again, the first and second ends each have hook and pile fasteners secured thereon. The second securing strap is adapted to couple the splint to a portion of the user's hand and to be secured thereon by way of the hook and pile fasteners. A first rounded end cap is positioned over the first end of the resilient cover and is secured thereon by way of a friction fit. A second rounded end cap is positioned over the second end of the resilient cover and is secured thereon by way of a friction fit.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved deformable splint which have all the advantages of the prior art splints and none of the disadvantages.

It is another object of the present invention to provide a new and improved deformable splint which may be easily and efficiently manufactured and marketed.

It is a further object of the present invention to provide new and improved deformable splint which is of durable and reliable constructions.

An even further object of the present invention is to provide a new and improved deformable splint which is susceptible of a low cost of manufacture with regard to both materials and labor, and which accordingly are then susceptible of low prices of sale to the consuming public, thereby making such deformable splint economically available to the buying public.

Still yet another object of the present invention is to provide a new and improved deformable splint which provide in the apparatuses and methods of the prior art some of the advantages thereof, while simultaneously overcoming some of the disadvantages normally associated therewith.

Even still another object of the present invention is to provide a splint which may be deformed.

Lastly, it is an object of the present invention to provide new and improved deformable splint which is adapted for engagement with the hand of a user. In its broadest context, the present invention includes a wire which is surrounded by a cover of resilient material. As such, the splint can be deformed into any number of various shapes to enable it to be employed upon the hand of the user in a number of different configurations. The splint further includes a number of VELCRO™ straps which are employed in securing the splint to the hand of a user. The various components of the present invention, and the manner in which they interrelate, will be described in greater detail hereinafter.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a sectional view taken along line 5—5 of FIG. 5.

FIG. 6 is a view of the splint, end caps and straps.

The same reference numerals refer to the same parts through the various Figures.

DESCRIPTION OF THE PREFERRED EMBODIMENT

Figure 1:
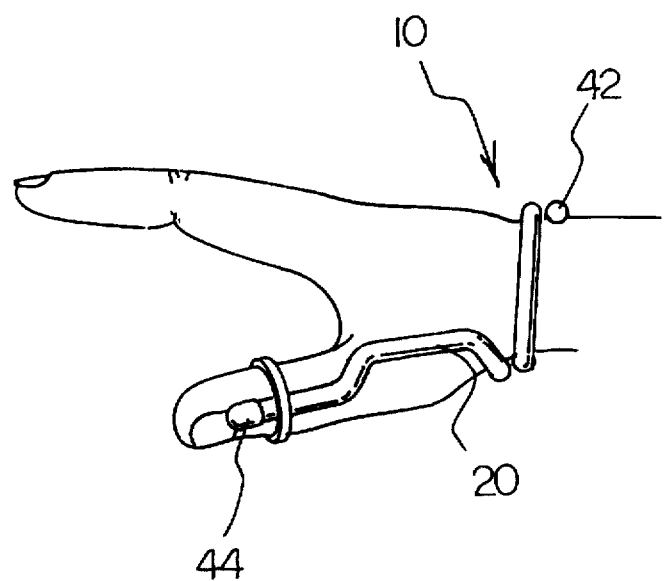
FIG. 1 is a view of the preferred embodiment of the deformable splint employed upon a hand in a first configuration.

With reference now to the drawings, and in particular to FIG. 1 thereof, the preferred embodiment of the new and improved deformable splint embodying the principles and concepts of the present invention and generally designated by the reference numeral 10 will be described.

The present invention relates to a deformable splint which is adapted for engagement with the hand of a user. In its broadest context, the present invention includes a wire which is surrounded by a cover of resilient material. As such, the splint can be deformed into any number of various shapes to enable it to be employed upon the hand of the user in a number of different configurations. The splint further includes a number of VELCRO™ straps which are employed in securing the splint to the hand of a user. The various components of the present invention, and the manner in which they interrelate, will be described in greater detail hereinafter.

The deformable splint 20 of the present invention is adapted for a variety of supporting configurations upon a user's hand. To achieve this the splint 20 includes a length of heavy gauge copper wire 22. As is best illustrated in FIG. 5, this length of wire 22 has a rectangular cross section. Additionally, the wire 22 is defined by a first end, a second end, and a intermediate extent therebetween. Although heavy gauge copper wire 22 has been described in conjunction with the preferred embodiment of the present invention other deformable materials in other gauges can be employed. The main requirement of the wire 22 is than it be both deformable and capable of maintaining its deformed shape.

A resilient cover 24 is employed to cover 24 the wire 22. The relationship between the wire 22 and resilient cover 24 is best illustrated in FIG. 5. In the preferred embodiment the cover 24 is constructed from neoprene. The cover 24 is positioned over, and covers the entire length of, the wire 22. The cover 24 includes a planar upper surface 26, a concave lower surface 28, two tapering side walls 32 and four rounded corners 34 interconnecting the side walls and upper and lower surfaces. This geometry of the cover 24 the cover 24 is best illustrated in reference to FIG. 5. The cover 24 is further defined by a first end, a second end and an intermediate extent therebetween. As with the wire 22, the main characteristic of the cover 24 is that it be deformable can capable of maintaining its deformed shape. This results in a splint 20 which can be bent into any shape desired by the user, and then bent again into a different shape at a later time. The materials of both the wire 22 and cover 24 are such that this process of bending and re-bending can be repeated several times.

In order to secure to splint 20 to the hand of a user, one or more VELCRO™ straps 36 are employed. In the preferred embodiment, two identical straps 36 are employed. Each of these straps 36 is defined by a first end, a second end and an intermediate extent therebetween. Additionally, the first and second ends of each strap have hook and pile fasteners 38 secured thereon. Either of the straps 36 are adapted to couple the splint 20 to a portion of the user's hand and to be secured thereon by way of the hook and pile fasteners 38.

Two rounded caps are employed to cover 24 the ends of the splint 20. Specifically, a first rounded end cap 42 is positioned over the first end of the resilient cover 24 and a second rounded end cap 44 is positioned over the second end of the resilient cover 24. Each of these covers, in the preferred embodiment is secured by way of a friction fit.

In use, the splint 20 is initially cut to the desired length. Then the end caps can be fictionally positioned upon the ends of the cover 24 and wire 22 to provide for smooth rounded end portions. The splint 20 can then be formed over the hand of the user in any one of a variety of configurations. Listed below are a few illustrative examples of how the splint 20 may be configured.

Thumb Splint

FIG. 1 illustrates the splint employed as a thumb support. This orientation is achieved by first wrapping the first end of the splint around the wrist of a user. The second end of the splint is then positioned along the thumb of the user. In this orientation, one VELCRO™ is employed to secure the second end of the splint to the thumb of the user.

Wrist Splint

Figure 2:
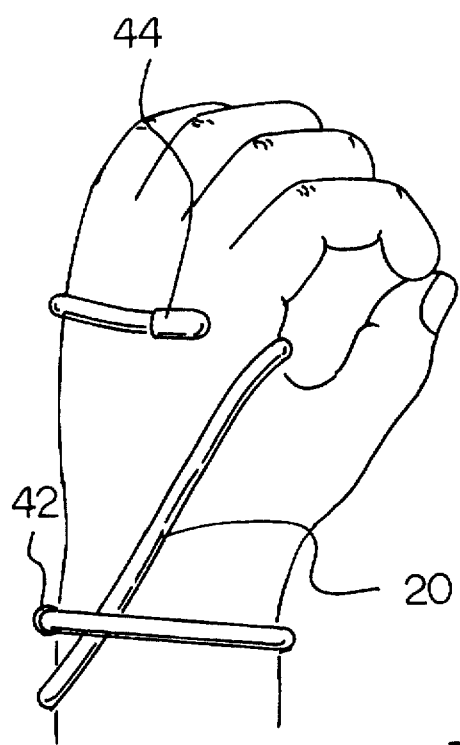
FIG. 2 is a view of the splint employed upon a hand in a second configuration.

FIG. 2 illustrates the splint employed as a wrist support. In this orientation, the first end of the splint is wrapped around the wrist of the user. The second end of the splint is then positioned over the top side of the hand and upon the upper portion of the palm. This orientation affords good wrist support and aids in healing a sprained wrist.

Finger Splint

Figure 3:
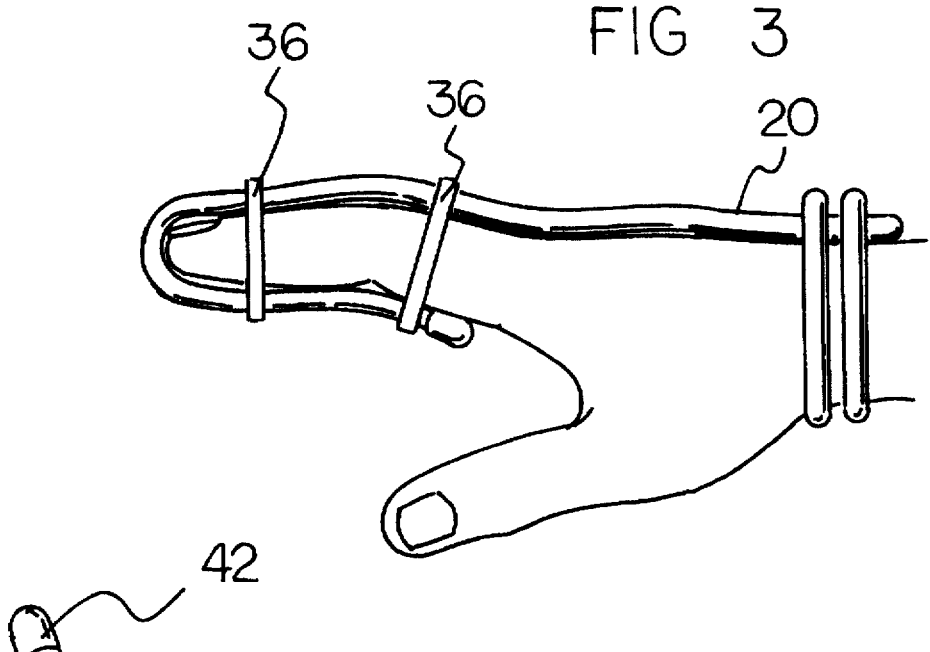
FIG. 3 is a view of the splint employed upon a hand in a third configuration.
Figure 4:
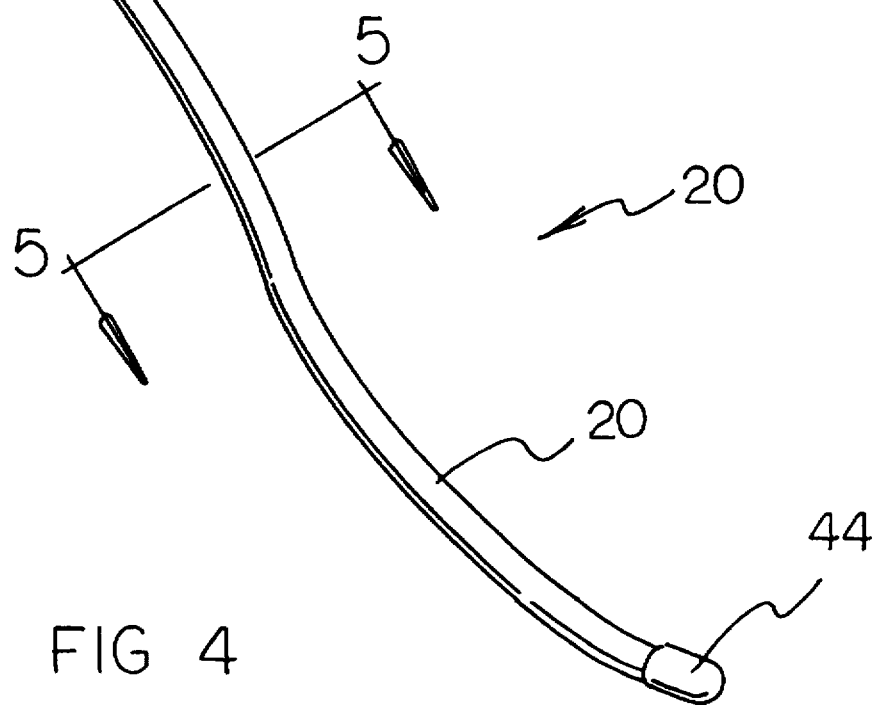
FIG. 4 is a perspective illustration of the splint.

FIG. 3 illustrates the splint employed as a finger support. In this orientation, the first end of the splint is wrapped around the wrist of the user. The second end of the splint is then positioned over top of one of the fingers and terminates at the underside of the finger adjacent the palm. Two, or more, VELCRO™ fasteners can be employed in this orientation to secure the second end of the splint to the user's finger.

These three orientations are only illustrative examples, and the splint of the present invention can be employed in any number of orientations.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A deformable splint adapted for a variety of supporting configurations upon a user's hand, the splint comprising in combination:

a length of heavy gauge copper wire, the length of wire having a rectangular cross section, a first end, a second end, and a intermediate extent therebetween;

a resilient cover constructed of neoprene, the positioned over and covering the entire length of the wire, the cover having an planar upper surface, a preformed concave concave lower surface, two tapering side walls and four rounded corners interconnecting the side walls and upper and lower surfaces, the cover further including a first end, a second end and an intermediate extent therebetween the lower concave surface allowing the cover to be securely positioned along the finger of a user;

a first securing strap having a first end, a second end and an intermediate extent therebetween, the first and second ends having hook and pile fasteners secured thereon, the first securing strap adapted to couple the splint to a portion of the user's hand and to be secured thereon by way of the hook and pile fasteners;

a second securing strap having a first end, a second end and an intermediate extent therebetween, the first and second ends having hook and pile fasteners secured thereon, the second securing strap adapted to couple the splint to a portion of the user's hand and to be secured thereon by way of the hook and pile fasteners;

a first rounded end cap positioned over the first end of the resilient cover and being secured thereon by way of friction;

a second rounded end cap positioned over the second end of the resilient cover and being secured thereon by way of friction.

2. A deformable splint adapted for a variety of supporting configurations upon a user's hand, the splint comprising in combination:

a length of wire, the length of wire having a rectangular cross section, a first end, a second end, and a intermediate extent therebetween;

a resilient cover positioned over and covering the entire length of the wire, the cover having an upper surface, a preformed concave lower surface, two side walls and four corners interconnecting the side walls and upper and lower surfaces, the cover further including a first end, a second end and an intermediate extent therebetween the concave lower surface allowing the cover to be securely positioned along the finger of a user;

a first securing strap having a first end, a second end and an intermediate extent therebetween, the first and second ends having hook and pile fasteners secured thereon, the first securing strap adapted to couple the splint to a portion of the user's hand and to be secured thereon by way of the hook and pile fasteners;

a second securing strap having a first end, a second end and an intermediate extent therebetween, the first and second ends having hook and pile fasteners secured thereon, the second securing strap adapted to couple the splint to a portion of the user's hand and to be secured thereon by way of the hook and pile fasteners.

3. The splint as described in claim 2 wherein:

the wire is a heavy gauge copper wire; and the resilient cover is constructed from neoprene.

4. The splint as described in claim 2 further comprising:

a first rounded end cap positioned over the first end of the resilient cover and being secured thereon by way of friction;

a second rounded end cap positioned over the second end of the resilient cover and being secured thereon by way of friction.

5. The splint as described in claim 2 wherein:

the upper surface of the cover is planar, the lower surface of the cover is concave, the two side walls are tapered, the four corners interconnecting the upper surface, the lower surface and two side walls are rounded.

* * * * *